United States Patent [19]

Weinert

[11] 4,219,770
[45] Aug. 26, 1980

[54] INSERTION LOSS AND PHASE SHIFT MEASUREMENT SYSTEM AND METHOD

[75] Inventor: Fritz K. Weinert, Gaithersburg, Md.

[73] Assignee: Weinschel Engineering Co., Inc., Gaithersburg, Md.

[21] Appl. No.: 2,585

[22] Filed: Jan. 11, 1979

[51] Int. Cl.² .................. G01N 27/04; H03B 3/04
[52] U.S. Cl. ........................... 324/58 A; 328/155
[58] Field of Search .............. 324/58 A, 58 R, 57 R; 364/482; 328/155, 133

[56] References Cited

U.S. PATENT DOCUMENTS 3,104,354  9/1963  Weinschel et al. ............ 324/58 A

OTHER PUBLICATIONS

White, D. E.; "A Computer-Operated . . ."; IEEE Trans. on Inst. & Measurement; vol. IM-25; No. 4; Dec. 1976; pp. 419-424.

*Primary Examiner*—Ernest F. Karlsen
*Attorney, Agent, or Firm*—Howard L. Rose

[57] ABSTRACT

Insertion loss measurement at microwave frequencies is achieved using an improved IF substitution technique wherein the IF test signal is applied to a feedback loop which generates a feedback signal to null out the test signal. A precision calibrated attenuator in the path of the feedback signal is adjusted to achieve the null, and the difference between attenuator settings with the device under test in and out of the microwave test signal path is a measure of the insertion loss of the device under test. In one embodiment the difference signal between the IF test signal and the fed back null signal is divided into amplitude and phase components which are integrated and used to control the attenuation and phase shift, respectively, of a reference signal at the IF test signal frequency, the controlled reference signal comprising the fed back null signal. In another embodiment the amplitude and phase components are filtered at d.c., restored to IF, and recombined before being fed back as the null signal. Still another embodiment steps the difference signal is stepped down to the audio frequency range in successive steps and is filtered at the audio level before being stepped back up to IF and fed back. Any of these embodiments can be employed in a dual channel system, one of which contains the device under test, wherein the fed back null signals are compared in phase to determine the phase shift introduced by the device under test. A novel phase shifter is disclosed wherein the 360° limitation of unambiguous phase detection is overcome.

25 Claims, 5 Drawing Figures

INSERTION LOSS AND PHASE SHIFT MEASUREMENT SYSTEM AND METHOD

TECHNICAL FIELD

The present invention relates to systems for measuring attenuation and/or phase of microwave components. More specifically, the present invention relates to improvements in the IF substitution method of microwave attenuation measurement whereby measurement is possible over a range of at least 0 to 120 dB. The frequency range of interest is from approximately 10 MHz to 18 GHz.

BACKGROUND ART

The IF substitution method of microwave attenuation or insertion loss measurement is very well known. In its broadest sense it involves converting a microwave test signal to some lower or intermediate frequency (IF), such as by heterodyning, so that the converted IF signal frequency remains the same for all measurements over the microwave frequency range of interest. An attenuation measurement at any one microwave frequency requires a first reading of the IF signal level with the device under test shorted out, and a second reading with the device under test in the microwave test signal path. The difference between these readings is a measure of the attenuation of the device under test. Utilization of a constant IF signal frequency avoids the problems inherent in using measuring arcuitry which inherently has frequency-dependent characteristics. However, a major problem with this basic approach is that it is limited to a small range of attenuation measurements by the gain limitations of any practical IF amplifier employed in the measurement circuitry. For example, it is desirable to permit attenuation measurements from 0 to 120 dB which corresponds to a range of one million to one. Early on it was suggested that a step attenuator be employed in series with the IF amplifier to reduce the amplifier gain requirements. However, even in such instances it was found that the amplifier characteristics tend to vary to an unacceptable degree.

In U.S. Pat. Nos. 3,034,045 (Weinschel) and 3,104,354 (Weinschel et al), there is disclosed an IF substitution technique which eliminates the critical aspects of the IF amplifier. In this arrangement, the IF signal derived from the microwave test signal and a reference IF signal of the same frequency, derived from a standard source, are fed in interlaced fashion to an IF amplifier. Any difference in amplitude between the two IF signals results in a square wave output from the IF amplifier at the interlacing frequency, nominally 1 KHz. A precision step attenuator, connected in series with the reference IF signal, is adjusted to equalize the two IF signal amplitudes and eliminate the square. The difference between the precision attenuator readings with the device under test in and out of the circuit is a measure of the attenuation of the device under test. During these readings, the gain characteristic of the IF amplifier is not critical since the only purpose of the amplifier is to detect the existence of a difference between the two IF signal levels. However, even with this sophisticated and widely accepted approach to the IF substitution technique, it has been found that 0 to 90 dB is the practical range of permitted attenuation measurement. The reason for the limitation is that below 90 dB system noise starts to interfere with measurement accuracy. The noise derives in part from the reference attenuator and in part from the switching required to interlace the IF signals. Some of this noise can be eliminated if turning the signal sources on and off rather than switching them through gates to achieve interlacing. However, many such sources do not operate well, both in terms of frequency stability and longevity, when repetitively turned on and off.

Another prior art IF substitution approach is described in a paper by Little et al entitled "An NBS Developed Network Analyzer" which appeared in the proceedings from the Conference on Precision Electromagnetic Measurements held in Boulder, Colorado from June 28 to July 1, 1976. In that system the converted IF signal, derived from the microwave test signal, is summed with quadrature components of the IF reference signal. These quadrature components are automatically adjusted until their vectorial sum is of equal magnitude and opposite phase to the converted IF signal. The procedure involves establishing successive estimates until the balance is achieved, whereupon a measure of attenuation is found from the ratio of reference signal adjustments required to achieve balance with and without the device under test in the line. The procedure requires use of a minicomputer and is very slow and cumbersome.

It is therefore an object of the present invention to provide an improvement in the IF substitution method of microwave attenuation measurement which permits simple and accurate measurement over a range of 0 to 120 dB.

It is another object of the present invention to provide an IF substitution method for measuring microwave attenuation and/or phase shift which is devoid of the aforementioned prior art problems.

DISCLOSURE OF INVENTION

In accordance with the present invention the IF reference signal is made adjustable in amplitude and phase so as to null out the converted IF test signal in a phase lock loop. The level of the amplitude and phase controlled IF reference signal is then a measure of the attenuation in the microwave test signal line. In one embodiment, in which the converted IF test signal and the IF reference signal are rendered phase coherent by means of a separate local oscillator loop, the two IF signals are compared and their amplitude difference signal is split into two quadrature components representing phase and amplitude. The phase component adjusts the phase of the IF reference signal in a novel phase shifter, while the amplitude component controls the amplitude of the IF reference signal via a variable attenuator, so that the phase and amplitude controlled reference signal nulls out the test signal. In a second embodiment, the two quadrature components are filtered and then summed together to achieve the nulling signal, thereby eliminating the need for the phase shifter and variable attenuator. In still another embodiment, the IF difference signal is converted down to audio frequency in successive heterodyne steps and filtering is achieved in the audio range before converting the signal back up to the IF range. This signal is used to null out the test signal. In this latter approach the local oscillator frequency control loop is eliminated since there is no need for phase coherence between the IF test signal and a reference signal. In all cases, the system can be operated with two identical channels and the output signals compared to provide a measurement of phase shift in the device under test.

A novel variable phase shifter overcomes the 360° unambiguous phase detection limitation by controlling a VCO at a higher frequency than that of the phase shifted signal.

BRIEF DESCRIPTION OF THE DRAWINGS

The above and still further objects, features and advantages of the present invention will become apparent upon consideration of the following detailed description of one specific embodiment thereof, especially when taken in conjunction with the accompanying drawings, wherein.

BEST MODE OF CARRYING OUT THE INVENTION

Figure 1:
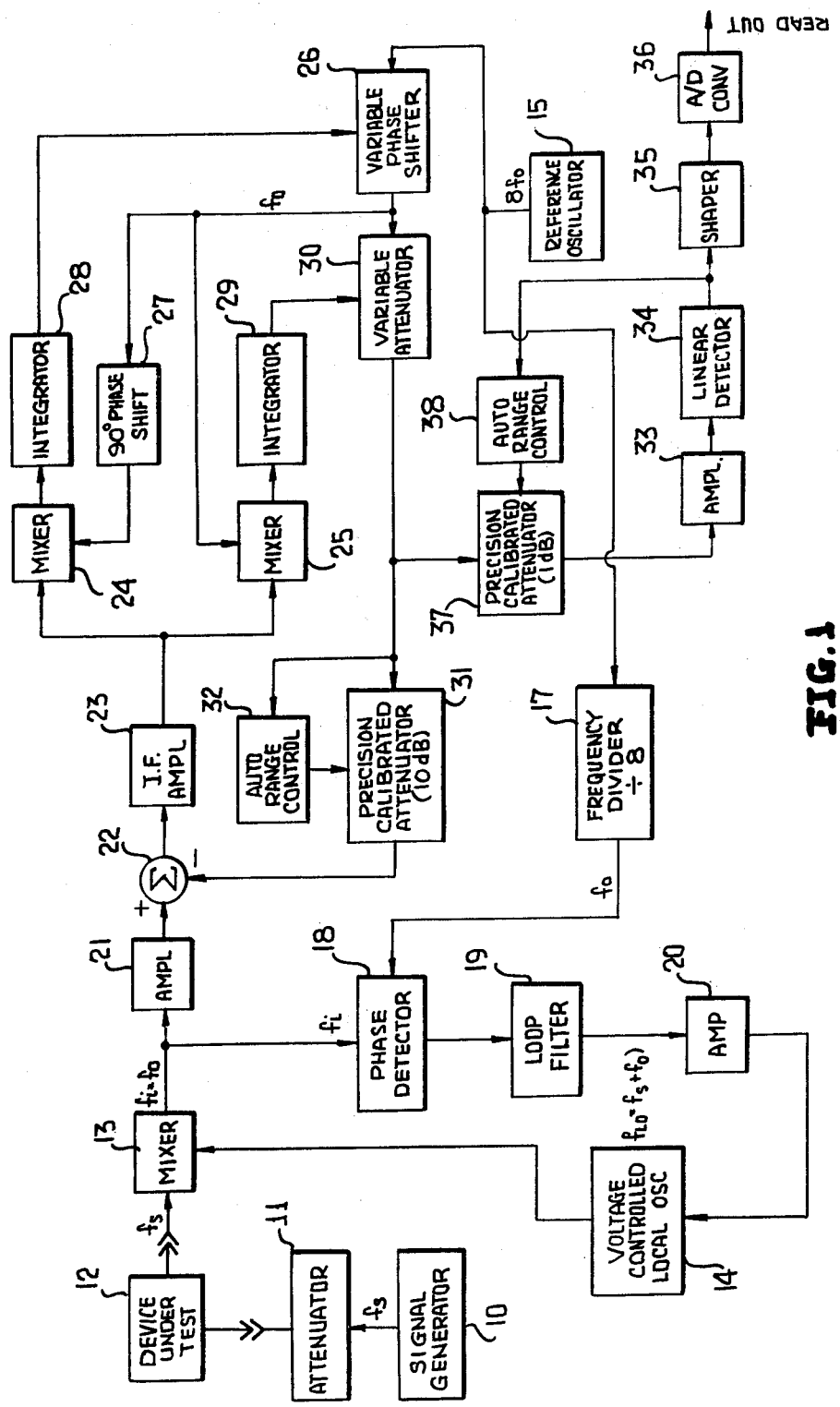
FIG. 1 is a circuit diagram of one embodiment of the insertion loss measuring system of the present invention.

Referring to FIG. 1, a signal generator 10 provides a microwave test signal at a frequency $f_s$ which is passed through an attenuator 11. The frequency $f_s$ of the microwave test signal is typically adjustable at generator 10 over the frequency range of interest. Attenuator 11 represents the source impedance of generator 10. The microwave test signal is passed through a device under test 12 which may be any microwave component having an insertion loss to be determined. As will be described below, the device under test 12 is readily by-passed (i.e. shorted) to permit alternative measurements with device 12 in and out of the signal path. The microwave test signal is then applied to one input terminal of a frequency conversion device such as mixer 13 which typically is a heterodyning circuit capable of providing an output signal at a frequency corresponding to the difference between the two applied frequencies. The second input signal for mixer 13 is derived from local oscillator 14 which is typically a voltage controlled oscillator providing a signal at the frequency $f_{LO}$. This latter frequency, $f_{LO}$, is equal to $(f_s+f_o)$, wherein $f_o$ is one-eighth the frequency of the reference output signal from a reference oscillator 15 to be described. The output signal from local oscillator 14 is applied to mixer 13. In the manner to be described below, the frequency of local oscillator 14 is controlled such that the difference frequency $f_i$ of the output signal from mixer 13 is equal to $f_o$ which is in the intermediate frequency (IF) range, nominally 1.25 MHz.

Reference oscillator 15 provides the reference signal at frequency $8f_o$, which signal is frequency-divided by a factor of eight at divider 17 and applied to a phase detector 18. A second input signal to the phase detector is the output signal from mixer 13 at frequency $f_i$. Phase detector 18 provides an output signal level proportioned to the phase difference between the two applied signals to loop filter 19. The filtered signal is amplified at amplifier 20 and then applied as a control signal to local oscillator 14. Elements 14, 13, 18, 19 and 20 are thus parts of a phase lock loop which serve to keep local oscillator 14 both frequency and phase locked to the frequency and phase of reference oscillator 15.

The output signal from mixer 13 is also amplified at amplifier 21 and then applied to a differencing circuit 22 where it is summed with the inversion of a feedback signal to be described below. The difference signal is amplified in IF amplifier 23, the output signal from which is delivered in parallel to mixers 24 and 25. The second input signals for these mixers are derived from reference oscillator 15, the signal from which is fed to a variable phase shifter 26 which is described in detail below with reference to FIG. 2. For the present discussion it is sufficient to state that phase shifter 26 incorporates a divide by eight frequency divider and shifts the phase of the frequency divided signal in proportion to the level of an applied control signal. The phase shifted signal, at frequency $f_o$, is applied directly to mixer 25 and to a 90° phase shift circuit 27. The 90° shifted signal is to mixer 24. Thus, the mixers 24 and 25 receive identical pairs of input signals except that one input signal of each pair differ in phase by 90°. The resulting output signals from mixers 24 and 25 are applied to integrators 28 and 29, respectively. The output signal from integrator 28 is used as the control signal to shift the phase of the signal passed through variable phase shifter 26. The output signal from integrator 29 is used to control the attenuation of a variable attenuator 30 which receives the output signal from variable phase shifter 26. The signal passed by attenuator 30 is applied to a precision calibrated attenuator 31 and then to differencing circuit 22 as the feedback signal. Precision calibrated attenuator 31 is an adjustable attenuator which selects attenuation levels in individual 10 dB steps over a wide range of attenuation. Such an attenuator is described in my prior U.S. patent application Ser. No. 801,873, filed May 31, 1977, and entitled ATTENUATOR WITH COMPENSATION OF IMPEDANCE ERRORS, which patent application is expressly incorporated herein by reference. An automatic range control circuit 32 is associated with attenuator 31 to automatically bring the total attenuation into the proper 10 dB range as the applied signal level varies. The output signal from variable attenuator 30 is also fed to a metering circuit including a precision calibrated attenuator 37, amplifier 33, detector 34, signal shaper 35 and analog to digital converter 36 from which a digital readout is provided to represent the level of the output signal from variable attenuator 30. Precision calibrated attenuator 37 is similar to attenuator 31, but is calibrated in 1 dB steps. An automatic range control circuit 38 responds to the output level from detector 34 to automatically adjust attenuator 37 in 1 dB steps and thereby keep the detector level constant within 1 dB.

An important aspect of the present invention is the nulling of the IF test signal and using the nulling signal as a measure of the insertion loss or attenuation in the microwave test signal path. In the embodiment of FIG. 1, nulling is advantageously achieved by breaking the difference signal into quadrature-related amplitude and phase components which are used to adjust the amplitude and phase, respectively, of the nulling signal.

Performing an insertion loss measurement with the embodiment of FIG. 1 proceeds as follows. The device under test 12 is initially shorted out, as by a coaxial cable or the like, and signal generator 10 is set to the desired frequency. The microwave signal at frequency $f_s$ is passed through the shorted line, converted to intermediate frequency $f_i$ at mixer 13, and passed onto differencing circuit 22. The difference signal between the IF test signal and the fedback IF reference signal is fed to IF amplifier 23. Importantly, since the function of the feedback in this loop is to null out the IF test signal, the IF amplifier always receives a very low level signal, always at the same IF frequency $f_i$, so that there are no inaccuracies introduced by amplifier gain variations due to changing frequency or changing signal level. The output signal from IF amplifier 23 is broken down into an amplitude component at mixer 25 and a phase component at mixer 24. The phase component is smoothed at integrator 28 and used to control the phase of the reference signal at phase shifter 26. The amplitude component is smoothed by integrator 29 and used to control the amplitude of the reference signal at variable attenuator 30. The output signal level from attenuator 30 is sensed by the automatic range control circuit 32 to adjust the setting of precision calibrated attenuator 31 in 10 dB steps until the output signal from attenuator 31 falls within a predetermined range. The output levels from integrators 28 and 29 respond accordingly, changing until an equilibrium is reached, whereupon the output voltage from attenuator 30 corresponds to the substituted IF voltage times the attenuation factor of precision attenuator 31. That is, the substituted IF voltage applied to differencing circuit 22 by attenuator 31 is related to the output level from attenuator 30 by the precisely known attenuation factor of attenuator 31 which is easily read out. This output level from attenuator 30 is automatically attenuated in 1 dB steps at attenuator 37 and then measured and read out at A/D converter 36. The settings of precision attenuators 31 and 37 and the level read out from A/D converter 36 are noted. The test is then repeated with the device under test 12 inserted in the microwave test signal line. Precision attenuators 31 and 37 once again are adjusted until the predetermined reference level range is obtained. Then, once again, the level read out from A/D converter 36 is noted. The differences between the first and second settings of the precision attenuators 31 and 37 and the first and second readings at A/D converter 36 correspond to the insertion loss of the device under test at the microwave test frequency $f_s$. Of course, $f_s$ can be changed to permit multiple insertion loss measurements over the frequency band of interest.

In order to show mathematically that the measurement technique is correct, it is noted that the output signal from variable attenuator 30 operates within the overall nulling feedback loop in a manner so as to attempt to null out the IF test signal from amplifier 21. This attempt to null is made irrespective of the setting of precision attenuator 31. If we assume that the IF test signal level applied to differencing circuit 22 is x, then with the operation of the nulling loop as described, the output signal level from the precision attenuator 31 will also be x. If the attenuation factor of precision attenuator is A, then the signal y applied to the attenuator 37 can be represented as x/A. In the following description, $x_1$, $y_1$ and $A_1$ represent the signal levels and precision attenuation factor present during the measurement taken with the device under test shorted; $x_2$, $y_2$ and $A_2$ represent the same parameters for the measurement taken with the device under test in the line. Thus, $y_1 = x_1/A_1$, and $y_2 = x_2/A_2$. The values $y_1$ and $y_2$ are read by A/D converter 36. Then, $x_1/x_2 = y_1 A_1 / y_2 A_2$. The ratio of the attenuation factors used in the two measurements is therefore proportional to the ratio of the IF test signal levels present in the two measurements. If the measurement is made in dB, as in the present case of interest, log $x_1$ − log $x_2$ = log $y_1$ − log $y_2$ + log $A_1$ − log $A_2$; or, the difference between the measured levels at A/D converter 36 plus the difference between the two attenuation factors (attenuators 31 and 37 combined) represents the insertion loss of the device under test.

With the contribution of IF amplifier 23 to measurement inaccuracies being reduced to nil, as described above, the major sources of measurement inaccuracy are the precision calibrated attenuators 31 and 37 and the A/D converter 36. However, the particular attenuator described above in my U.S. patent application Ser. No. 801,873 is extremely accurate, resulting in an accurate insertion loss measurement capability over a 0 to 120 dB range.

Figure 2:
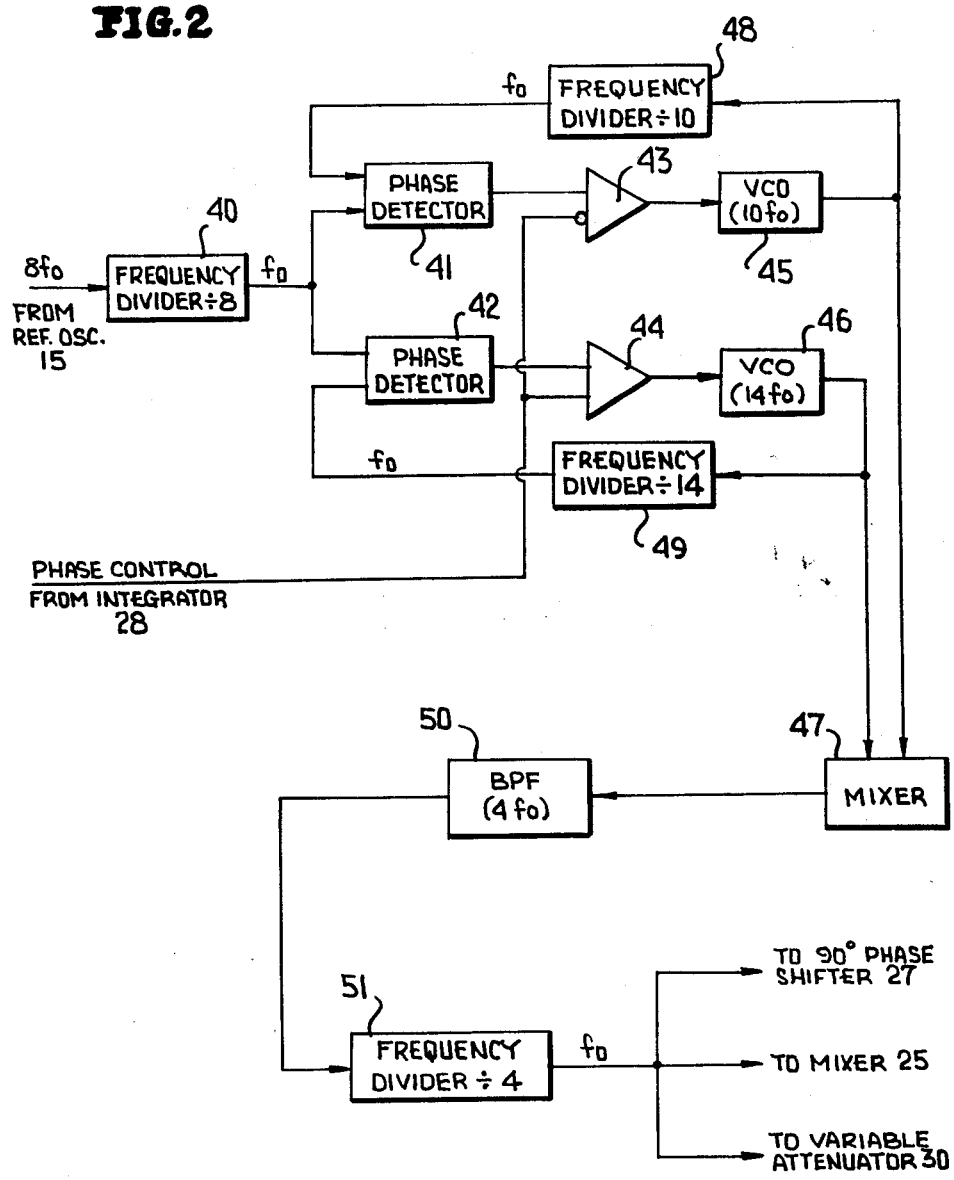
FIG. 2 is a circuit diagram of a novel variable phase shifter employed in the circuit of FIG. 1.

The variable phase shifter 26 is illustrated in greater detail in FIG. 2. Specifically, the IF reference signal, at frequency 8 $f_o$, is received at a frequency divider 40 which has a division factor of eight. The frequency divided signal is applied in parallel to two phase detectors 41 and 42 which, in turn, drive respective differential operational amplifiers 43 and 44. A second input signal to these amplifiers is the phase control signal derived from integrator 28 of FIG. 1, the phase control signal being inverted before being applied to amplifier 43 so that the two amplifiers are controlled in opposite senses by the same signal. The output signals from amplifiers 43 and 44 serve as phase control signals for voltage controlled oscillators (VCO's) 45 and 46, respectively. The frequency of VCO 45 is nominally 10 $f_o$; the frequency of VCO 46 is nominally 14 $f_o$. The output signals from VCO's 45 and 46 are fed to a mixer 47 from which the difference frequency 4$f_o$, is derived. In addition, each VCO output signal is fed to a respective frequency divider. Frequency divider 48 has a division factor of ten and feeds its output signal to phase detector 41. Frequency divider 49 has a division factor of 14 and feeds its output signal back to phase detector 42.

The output signal from mixer 47 is passed through a bandpass filter 50, which is tuned to 4$f_o$, and then to a divide-by-four frequency divider 51. The output signal from frequency divider 51 is fed to 90° phase shifter 27, mixer 25 and variable attenuator 30, all of FIG. 1.

The function of the phase control signal from integrator 28 (FIG. 1) is to shift the phase of the reference signal in phase shifter 26 as required to achieve a null at differencing circuit 22. The simplistic approach of using a VCO for the reference oscillator 15 and then controlling the oscillator phase with the phase control signal is not useful since the IF reference frequency must be constant and must be phase coherent with the IF test signal. Therefore, some sort of phase sensing arrangement must be used to control the reference signal in the nulling loop of FIG. 1. However, phase detectors or sensors are generally limited to being able to sense phase differences between 0° and ±360°, since phase differences greater than 360° produce ambiguous output signals. It is the function of the twin loop phase shifter of FIG. 2 to overcome this 360° limitation. This will be evident from the following description of the phase shifter operation.

Phase detector 41 provides an output signal with a level proportional to the phase difference (within ±360°) between the signals from dividers 40 and 48. This level is amplified and used to control VCO 45 which operates at ten times the frequency $f_o$ of the signals sensed at phase detector 48. Thus, a phase difference at phase detector 41 (e.g. 180°) results in a change of ten times that difference (e.g. 1800°) in the phase of the output signal from VCO 45. By frequency dividing this output signal back to $f_o$ at divider 48, this amplification of phase shift is achieved while operating within the 360° limitation of phase detector 41. Similarly, the other loop, including VCO 46, achieves a multiplication factor of fourteen for the phase difference detected at phase detector 42.

The function of the phase control signal from integrator 28 is to insert a shift into the phase of VCO's 45 and 46 proportional to the phase component of the null error signal provided by IF amplifier 23. This phase shift is in opposite senses at the two VCO's so that the net effect is additive at mixer 47. Therefore, the net phase control permissible in the $4f_o$ signal at bandpass filter 50 is $(10 \times 360°) + (14 \times 360°) = \pm 8640°$. After frequency division by four at divider 51 the net phase shift in the $f_o$ signal is $\pm 2160°$. It is clear, however, that by using this method of expanding phase shift range, substantially any phase shift can be achieved. It should be noted that, as a practical matter, most phase detectors are limited to detecting phase differences over a range somewhat smaller than $\pm 360°$, usually $\pm 300°$, wherefore the expanded phase shift range is similarly limited.

Figure 3:
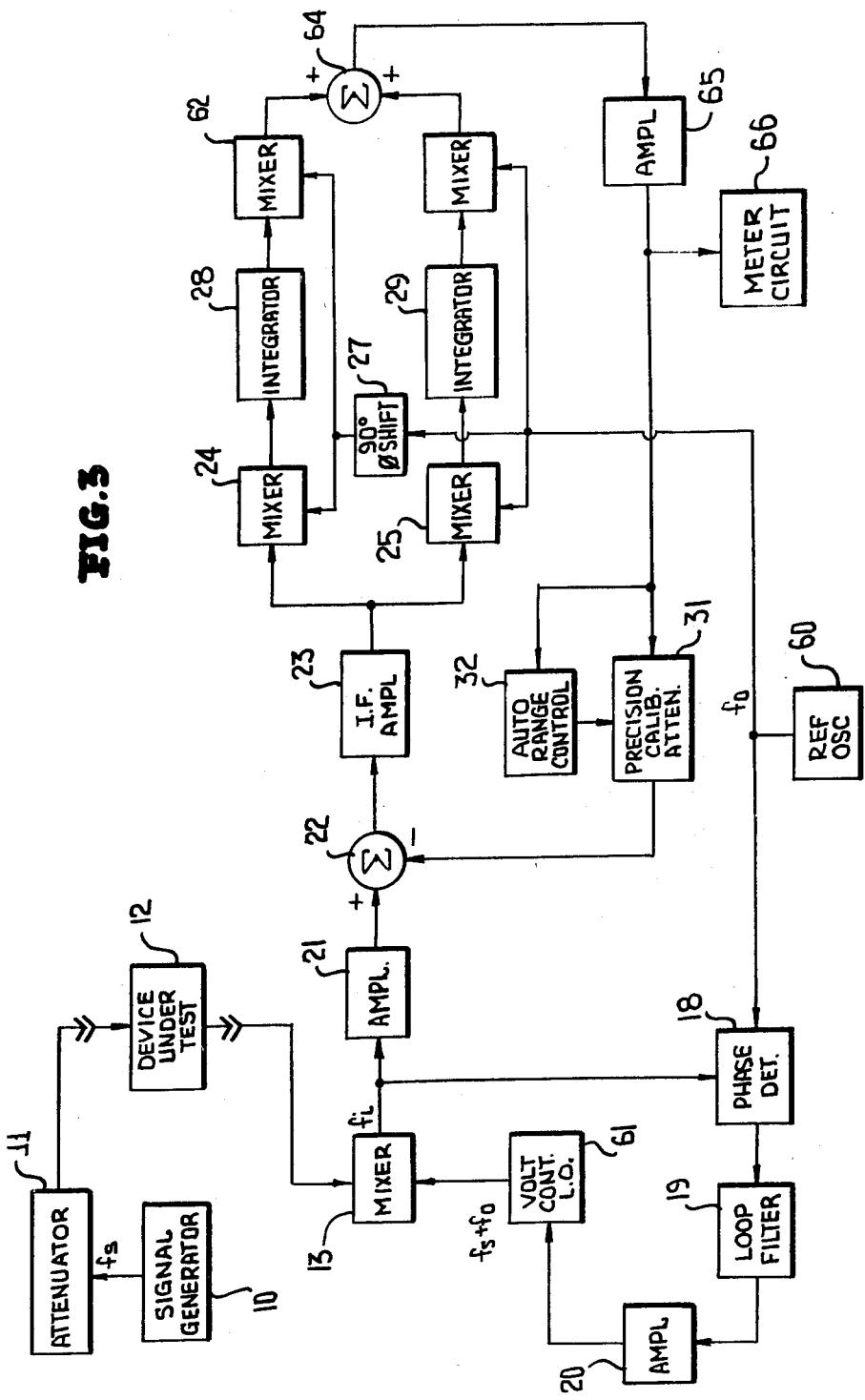
FIG. 3 is a circuit diagram of another embodiment of the insertion loss measuring system of the present invention.

An alternative embodiment of the insertion loss measuring system is illustrated in FIG. 3. Components appearing in both of the systems of FIGS. 1 and 3 are designated by the same reference numerals for ease of reference and simplicity of description. At the outset it is noted that the frequency of reference oscillator 60 and the nominal frequency of the local oscillator 61 in FIG. 3 is $f_o$ rather than $8f_o$ as used in FIG. 1. This is to illustrate that either $f_o$ or some multiple thereof can be used in either of these two embodiments. The major difference in the FIG. 3 embodiment is the fact that it is the error signal itself which is processed and fed back to differencing circuit 22 to seek a null rather than the reference signal controlled by the error signal as in the FIG. 1 embodiment. In this regard, the reference oscillator signal at frequency $f_o$ is fed directly to mixer 25 and to 90° phase shifter 24. Further, the output signals from integrators 28 and 29 are fed to additional mixers 62 and 63, respectively. Mixer 63 also receives the reference oscillator signal which is modulated by the output signal from integrator 29. Likewise, mixer 62 receives the output signal from 90° phase shifter 27 which is modulated by the output signal from integrator 28. The two modulated signals are summed at summing circuit 64, amplified at amplifier 65 and passed to the precision calibrated attenuator 31. Meter circuit 66 corresponds to elements 33, 34, 35 and 36, 37 and 38 of FIG. 1.

The difference in operation of the system of FIG. 3 resides primarily in the nulling loop. The phase component of the null signal applied to mixer 24 is restored at the output of mixer 62 after it has been filtered by integrator 28. Likewise, the amplitude component is restored at mixer 63 after it has been filtered by integrator 29. The filtering is thus done at d. c., rather than at the intermediate frequency, and the two quadrature components are summed before being amplified and fed back to achieve the desired null. This approach eliminates the need for the variable phase shifter. Moreover, since the filtering is done at d.c., the integrators need only be single-pole filters which nevertheless have the effect of narrow band filters.

Figure 4:
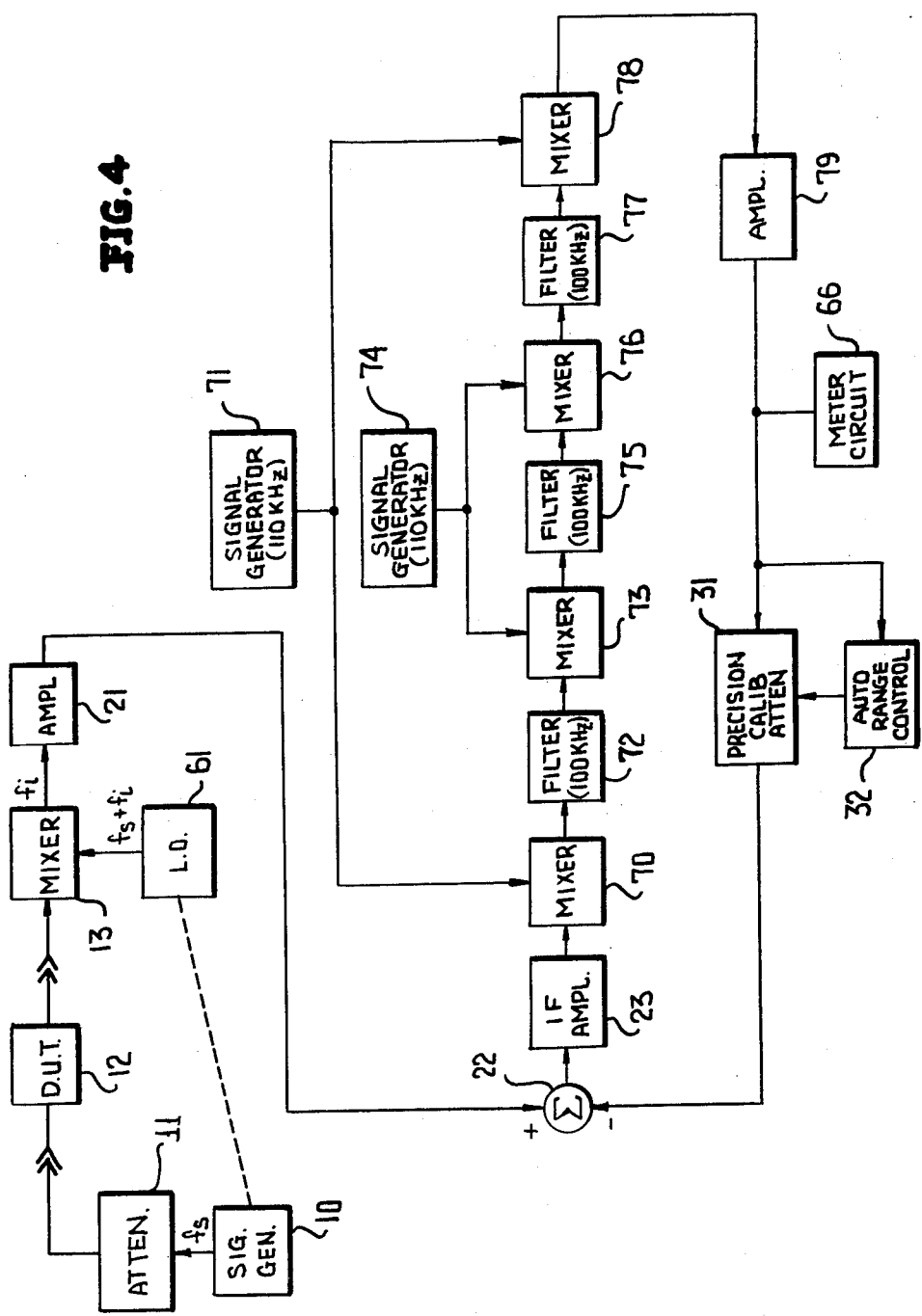
FIG. 4 is a circuit diagram of still another embodiment of the insertion loss measuring system of the present invention.

The system of FIG. 4 performs the same insertion loss measurements as the systems of FIGS. 1 and 3 but does not require phase coherence between the nulled IF signals. This permits elimination of the local oscillator loop employed in the systems of FIGS. 1 and 3. Referring specifically to FIG. 4, components therein which are the same or similar to components in FIGS. 1 or 3 are designated by the same reference numerals. Local oscillator 61, having the nominal frequency $f_s + f_i$, is commonly controlled with microwave signal generator 10 to assure that the output of mixer 13 is at the desired intermediate frequency $f_i$. Once again, the primary difference between this embodiment and those previously described resides in the nulling loop. The output signal from IF amplifier 23 is fed to a mixer 70 which also receives a signal from signal generator 71. The frequency of the signal from generator 71 is $f_i + 100$ KHz so that one of the components of the output signal from mixer 70 is at 100 KHz. A narrow band filter 72, tuned to 100 KHz, passes this component to a further mixer 73. This mixer also receives a 110 KHz signal from generator 74 so that a 10 KHz signal component is provided by mixer 73. A narrow band filter 75, tuned to 10 KHz, passes this signal component to mixer 76 which also receives the 110 KHz signal from generator 74. The difference frequency component of the two signals at mixer 76 is applied to narrow band filter 77 which is tuned to 100 KHz. The 100 KHz output signal from filter 77 is fed to a mixer 78 which also receives the $f_i + 100$ KHz signal from generator 71 and provides a signal at $f_i$. This signal is amplified at amplifier 79 and passed meter circuit and precision calibrated attenuator 31.

In the FIG. 4 embodiment the filtering is done at audio frequencies, rather than at IF, so that filter cost is relatively low. The filtered error signal is fed back to achieve the null at differencing circuit 22. Measurements are performed in the same way as described above in relation to FIGS. 1 and 3.

Figure 5:
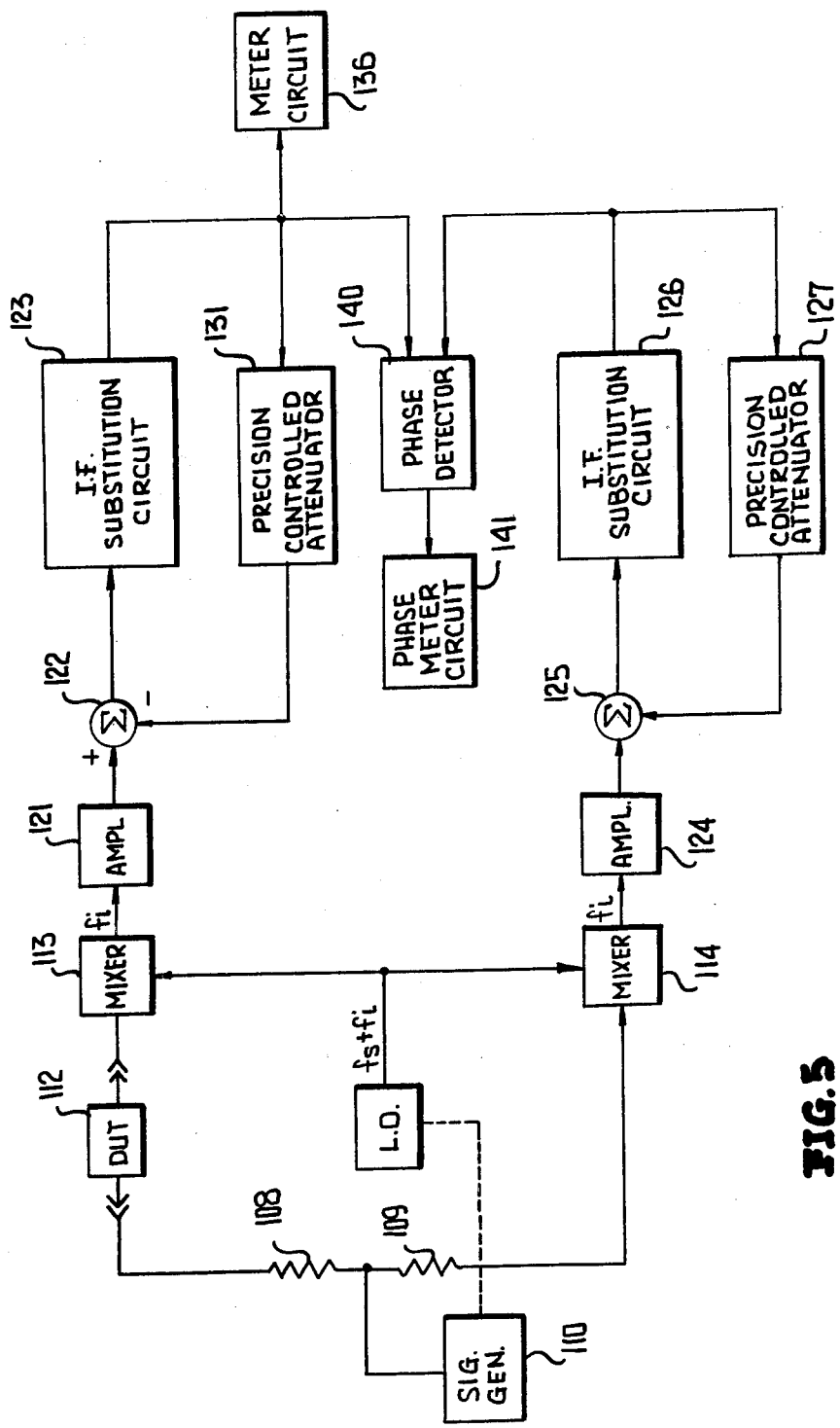
FIG. 5 is a circuit diagram of dual channel arrangement useful with the embodiments of FIGS. 1 or 3 to permit phase shift measurement.

Any of the systems of FIGS. 1, 3 and 4 may be used in a dual channel arrangement, such as illustrated in FIG. 5, to permit measurement of either insertion loss of phase shift introduced by a device under test. A microwave signal generator 110 passes a signal at frequency $f_s$ through a precision power splitter comprising resistors 108 and 109. The signal passing through resistor 108 is applied to the device under test 12 and then to mixer 113 which also receives a signal from local oscillator 116 having a frequency $f_s + f_1$. The difference frequency component, $f_i$, is amplified at amplifier 121 and applied to differencing circuit 122. The output signal from differencing circuit 122 is applied to an IF substitution circuit 123 (such as: elements 23–30 of FIG. 1; elements 23–25, 27–29, 62–65 of FIG. 3; or elements 23, 70–79 of FIG. 4). The IF substitution circuit 123 serves to process the error signal to provide a nulling feedback signal representative of the phase and amplitude correction required to achieve a null in the output signal from differencing circuit 122. This feedback signal is applied to precision calibrated attenuator 131 (which may have an automatic ranging circuit associated therewith) which in turn feeds the differencing circuit 122. The output signal from IF substitution circuit 123 is also applied to metering circuit 136 which is similar to metering circuit 66 of FIG. 3. The circuit as thus far described is capable of performing the insertion loss measurement procedure described in relation to FIGS. 1, 3 and 4.

The other channel of the system in FIG. 4 includes resistor 109 which passes the microwave signal at frequency $f_s$ from generator 110 to a mixer 114. The other signal supplied to mixer 114 is the signal from local oscillator 116 at frequency $f_s+f_i$. The difference frequency component $f_i$ is passed to amplifier 124 and then to differencing circuit 125. The output signal from this differencing circuit is applied to an IF substitution circuit 126, identical to circuit 123, and then to a precision calibrated attenuator 127 which feeds the nulling signal back to differencing circuit 125. This second channel is identical to the first channel in all respects except for the presence of device under test 112 in the first channel.

The output signals from the two IF substitution circuits 123 and 126 are applied to a phase detector 140. The phase detector provides an output signal to a phase meter circuit which registers the phase difference between the two null-correcting signals from circuits 123 and 126. Since the two channels are identical except for the device under test, the phase difference between these two null-correcting signals is representative of the phase shift introduced by the device under test. Thus, the dual channel arrangement is capable of measuring the insertion loss of the device under test, by using only one channel, and of measuring the phase shift through the device under test by using both channels.

The insertion loss and phase shift measuring system described herein are capable of performing measurements with relatively inexpensive and single components and are capable of performing these measurements quickly and accurately. Moreover, insertion loss measurements from 0 to 120 dB and beyond are possible with the present invention because: (1) the IF amplifier is operated at extremely low levels (i.e. virtually null) so that distortions in the amplifier response do not come into play; and (2) there is no switching or noisy reference attenuator to introduce noise into the low level insertion loss measurements.

The system of the present invention, for example, the embodiment of FIG. 1, may be sold in one comprehensive package including all of the components illustrated in FIG. 1 except, of course, the device under test 12. More often, however, the signal generator 10 and attenuator 11 will not be part of the package to reduce the cost and also because such generators are commonly available in any properly equipped laboratory in which testing at microwave frequencies is required. Likewise, mixer 13 and local oscillator 14 (and even frequency divider 116, when used) may be part of separate test equipment rather than the overall package. The systems described herein are useful in testing the output impedance characteristics of microwave signal generator over their operating frequency range. Under such circumstances the device under test is not in the line and the tests are made at different frequency settings of the generator to determine how the generator output impedance varies with frequency.

It is to be noted that precision calibrated attenuator 31 of FIGS. 1, 3 and 4 is highly accurate but has discrete or digital settings as opposed to being settable over a continuous or analog range. It should be noted that an analog attenuator, accurately operable over the desired 0 to 120 dB range, could replace attenuator 31 and thereby change and simplify the measurement technique somewhat. Specifically, such an analog attenuator would permit attenuator 37 to be eliminated. Each measurement would then be made by adjusting the analog attenuator until a predetermined level is read out from A/D converter, this level being the same for both the measurement with the device under test in the circuit and the measurement with the device under test out of the circuit. The insertion of the device under test would then be obtained by merely taking the difference between the two readings of the analog precision attenuator.

While I have described and illustrated one specific embodiment of my invention, it will be clear that variations of the details of construction which are specifically illustrated and described may be resorted to without departing from the true spirit and scope of the invention as defined in the appended claims.

I claim:

1. A system for measuring level changes in a microwave signal comprising:

means for providing said microwave signal;

local oscillator means for providing a local oscillator signal having a frequency which differs from the frequency of said microwave signal by a predetermined intermediate frequency;

mixer means for receiving said microwave signal and said local oscillator signal and providing a test signal at said intermediate frequency;

a feedback loop for nulling said test signal, said feedback loop comprising:

signal comparison means for comparing said test signal with a nulling signal to provide an error signal at said predetermined intermediate frequency representing the phase and amplitude difference between said test and nulling signals;

intermediate frequency amplifier means for amplifying said error signal;

control means responsive to the amplified error signal for providing a feedback signal which varies in accordance with variations in said error signal; and adjustable precision calibrated attenuator means for attenuating said feedback signal to provide said nulling signal to said signal comparison means; and metering means for monitoring said feedback signal.

2. The system according to claim 1 wherein said control means comprises:

reference oscillator means for providing a reference signal at said intermediate frequency;

a first mixer for beating said amplified error signal with said reference signal to provide a first beat frequency signal;

a phase shifter for shifting the phase of said reference signal by 90° to provide a phase-shifted reference signal;

a second mixer for beating said amplified error signal with said phase-shifted reference signal to provide a second beat frequency signal;

a first integrator for integrating said first beat frequency signal;

a second integrator for integrating said second beat frequency signal;

signal adjusting means for receiving said reference signal and varying the phase and amplitude thereof as a function of the integrated first and second beat frequency signals, the phase and amplitude-varied reference signal corresponding to said feedback signal.

3. The system according to claim 2 wherein said signal adjusting means comprises:

variable phase shifter means for shifting the phase of said reference signal as a function of said second beat frequency signal;

variable attenuation means for varying the amplitude of the phase-shifted reference signal as a function of said first beat frequency signal to provide said feedback signal.

4. The system according to claim 3 wherein said phase shifter comprises:

a first voltage controlled oscillator (VCO) having a nominal frequency which is a first multiple greater than said intermediate frequency;

a second VCO having a nominal frequency which is a second multiple greater than said intermediate frequency;

mixer means for receiving the output signals from said first and second VCO's and providing a further signal having a frequency which is the difference between the two VCO frequencies;

output frequency divider means, having a division factor equal to the difference between said first and second multiples, for dividing the frequency of said further signal by said division factor to provide an output signal from said phase shifter;

first feedback frequency divider means, having a division factor equal to said first multiple, for receiving the output signal from said first VCO and frequency-dividing same to provide a first frequency-divided signal;

second feedback frequency-divider means, having a division factor equal to said second multiple, for receiving the output signal from said second VCO and frequency-dividing same to provide a second frequency-divided signal;

a first phase detector for providing a first control signal at a level which is a function of the phase difference between said reference signal and said first frequency divided signal;

a second phase detector for providing a second control signal at a level which is a function of the phase difference between said reference signal and said second frequency-divided signal;

means for adjusting the frequency of said first VCO as a function of the level of said first control signal; and means for adjusting the frequency of said second VCO as a function of the level of said second control signal.

5. The system according to claim 4 further comprising means for applying said second frequency signal in opposite senses to said first and second VCO's to control the frequencies thereof.

6. The system according to claim 1 wherein said control means comprises:

reference oscillator means for providing a reference signal at said intermediate frequency;

a first mixer for beating said amplified error signal with said reference signal to provide a first beat frequency signal;

a phase shifter for shifting the phase of said reference signal by 90° to provide a phase-shifted reference signal;

a second mixer for beating said amplified error signal with said phase-shifted reference signal to provide a second beat frequency signal;

a first integrator for integrating said first beat frequency signal;

a second integrator for integrating said second beat frequency signal;

a third mixer for modulating said phase shifted reference signal with the integrated second beat frequency signal;

a fourth mixer for modulating said reference signal with the integrated first beat frequency signal;

means for summing the two modulated signals from said third and fourth mixers to provide said feedback signal.

7. The system according to claims 2, 3, or 6 wherein said local oscillator means is a voltage controlled oscillator (VCO), said system further comprising:

phase detector means for providing a phase lock signal having a level which is a function of the phase difference between said reference signal and said test signal;

loop filter means for filtering said phase lock signal; and means for applying the output signal from said loop filter as a frequency control signal to said local oscillator means VCO.

8. The system according to claim 1 wherein said control means comprises:

a first reference oscillator for providing a first reference signal having a frequency which is lower than the frequency of said test signal by a first predetermined number;

mixer means for beating said error signal with said first reference signal to provide a first signal having a frequency equal to said predetermined number;

first narrow band filter means, tuned to the frequency of said first signal, for filtering said first signal;

a second reference oscillator for providing a second reference signal having a frequency which is lower than the frequency of said first signal by a second predetermined number;

mixer means for beating said second reference signal with the filtered first signal to provide a second signal having a frequency equal to said second predetermined number;

second narrow band filter means, tuned to the frequency of said second signal, for filtering said second signal;

mixer means for mixing said second reference signal with the filtered second signal to provide a third signal having a frequency equal to the sum of the frequencies of said second signal and second reference signal;

third narrow band filter means, tuned to the frequency of said third signal, for filtering said third signal; and mixer means for mixing said first reference signal with the filtered third signal to provide said feedback signal.

9. The system according to claims 1, 2, 3, 6 or 8 wherein said means for providing a microwave signal includes a signal generator for providing a microwave test signal for application to a device under test, said microwave signal being the microwave test signal after being passed by said device under test.

10. The system according to claim 9 further comprising:

a second channel including:

further mixer means for receiving said microwave test signal and said local oscillator signal and providing a dual test signal at said intermediate frequency;

a further feedback loop, substantially identical to said feedback loop, for nulling said dual test signal; and phase detector means for detecting the phase difference between said feedback signal and the corresponding signal in said identical feedback loop.

11. The system according to claim 10 further comprising metering means responsive to detected phase difference at said phase detector means for providing a visual indication of the phase shift introduced into said microwave test signal by said device under test.

12. The system according to claims 1, 2, 3, 6 or 8 wherein said metering means comprises:
further adjustable precision calibrated attenuator means for automatically attenuating said feedback signal to provide an output signal level within a narrow range of signal levels; and
means for indicating said output signal level.

13. The system according to claim 12 wherein said adjustable precision calibrated attenuator means and said further adjustable precision calibrated attenuator means each include means for indicating their attenuation settings.

14. A method for measuring level changes in a microwave signal comprising the steps of:
providing said microwave signal;
providing a local oscillator signal having a frequency which differs from the frequency of said microwave signal by a predetermined intermediate frequency;
mixing said microwave signal and said local oscillator signal and providing a test signal at said intermediate frequency;
nulling said test signal, by the steps of:
comparing said test signal with a nulling signal to provide an error signal at said predetermined intermediate frequency representing the phase and amplitude difference between said test and nulling signals;
amplifying said error signal;
providing a feedback signal which varies in accordance with variations in said amplified error signal; and
attenuating said feedback signal to provide said nulling signal to said signal comparison means; and
monitoring said feedback signal.

15. The method according to claim 14 wherein the step of providing a feedback signal comprises:
providing a reference signal at said intermediate frequency;
beating said amplified error signal with said reference signal to provide a first beat frequency signal;
shifting the phase of said reference signal by 90° to provide a phase-shifted reference signal;
beating said amplified error signal with said phase-shifted reference signal to provide a second beat frequency signal;
integrating said first beat frequency signal;
integrating said second beat frequency signal;
varying the phase and amplitude of said reference signal as a function of the integrated first and second beat frequency signals, the phase and amplitude-varied reference signal corresponding to said feedback signal.

16. The method according to claim 15 wherein the step of varying the phase and amplitude comprises:

shifting the phase of said reference signal as a function of said second beat frequency signal; and
varying the amplitude of the phase-shifted reference signal as a function of said first beat frequency signal to provide said feedback signal.

17. The method according to claim 14 wherein the step of providing a feedback signal comprises:
providing a reference signal at said intermediate frequency;
beating said amplified error signal with said reference signal to provide a first beat frequency signal;
shifting the phase of said reference signal by 90° to provide a phase-shifted reference signal;
beating said amplified error signal with said phase-shifted reference signal to provide a second beat frequency signal;
integrating said first beat frequency signal;
integrating said second beat frequency signal;
modulating said phase-shifted reference signal with the integrated second beat frequency signal;
modulating said reference signal with the integrated first beat frequency signal; and
summing the two modulated signals to provide said feedback signal.

18. The method according to claims 15, 16 or 17 further comprising the steps of:
providing a phase lock signal having a level which is a function of the phase difference between said reference signal and said test signal;
filtering said phase lock signal; and
applying the filtered phase lock signal from said loop filter as a frequency control signal to control the frequency of said local oscillator.

19. The method according to claim 14 wherein the step of providing a feedback signal comprises:
providing a first reference signal having a frequency which is lower than the frequency of said test signal by a first predetermined number;
beating said error signal with said first reference signal to provide a first signal having a frequency equal to said predetermined number;
narrow band filtering said first signal;
providing a second reference signal having a frequency which is lower than the frequency of said first signal by a second predetermined number;
beating said second reference signal with the filtered first signal to provide a second signal having a frequency equal to said second predetermined number;
narrow band filtering said second signal;
mixing said second reference signal with the filtered second signal to provide a third signal having a frequency equal to the sum of the frequencies of said second signal and second reference signal;
narrow band filtering said third signal; and
mixing said first reference signal with the filtered third signal to provide said feedback signal.

20. The method according to claim 14 wherein the step of providing a microwave signal includes providing a microwave test signal for application to a device under test, said microwave signal corresponding to the microwave test signal after being passed by said device under test.

21. The method according to claim 20 further comprising:
receiving said microwave test signal and said local oscillator signal and providing a dual test signal at said intermediate frequency;

nulling said dual test signal in a substantially identical manner to the nulling of said test signal; and detecting the phase difference between said feedback signal and the corresponding signal used in nulling said dual test signal.

22. The method according to claim 21 further comprising the step of providing a visual indication of the phase shift introduced into said microwave test signal by said device under test.

23. A phase shifter for an input signal having a predetermined frequency comprising:

a first voltage controlled oscillator (VCO) having a nominal frequency which is a first multiple greater than said predetermined frequency;

a second VCO having a nominal frequency which is a second multiple greater than said predetermined frequency;

mixer means for receiving the output signals from said first and second VCO's and providing a further signal having a frequency which is the difference between the two VCO frequencies;

output frequency divider means, having a division factor equal to the difference between said first and second multiples, for dividing the frequency of said further signal by said division factor to provide an output signal from said phase shifter;

first feedback frequency divider means, having a division factor equal to said first multiple, for receiving the output signal from said first VCO and frequency-dividing same to provide a first frequency-divided signal;

second feedback frequency-divider means, having a division factor equal to said second multiple, for receiving the output signal from said second VCO and frequency-dividing same to provide a second frequency-divided signal;

a first phase detector for providing a first control signal at a level which is a function of the phase difference between said input signal and said first frequency divided signal;

a second phase detector for providing a second control signal at a level which is a function of the phase difference between said input signal and said second frequency-divided signal;

means for adjusting the frequency of said first VCO as a function of the level of said first control signal; and means for adjusting the frequency of said second VCO as a function of the level of said second control signal.

24. The phase shifter according to claim 23 further comprising control means for introducing a phase shift between said input and output signals by applying an additional control voltage to each of said first and second VCO's.

25. The phase shifter according to claim 24 wherein said control means comprises means for applying said additional control voltage in opposite senses to said first and second VCO's.

* * * * *